(12) United States Patent
Li et al.

(10) Patent No.: US 10,472,296 B2
(45) Date of Patent: Nov. 12, 2019

(54) COMPOSITE MICROORGANISM ENZYME, METHOD FOR PREPARING PLANT NUTRIENT SOLUTION BY USING COMPOSITE MICROORGANISM ENZYME, AND FERTILIZER SYNERGIST

(71) Applicant: Weihai Shidai Marine Biotechnology Co., Ltd., Weihai, Shandong Province (CN)

(72) Inventors: Jian Li, Weihai (CN); Mingtan Li, Weihai (CN)

( * ) Notice: Subject to any disclaimer, the term of this patent is extended or adjusted under 35 U.S.C. 154(b) by 120 days.

(21) Appl. No.: 15/503,685

(22) PCT Filed: Jan. 29, 2015

(86) PCT No.: PCT/CN2015/071860
§ 371 (c)(1),
(2) Date: Feb. 13, 2017

(87) PCT Pub. No.: WO2016/029646
PCT Pub. Date: Mar. 3, 2016

(65) Prior Publication Data
US 2017/0275213 A1    Sep. 28, 2017

(30) Foreign Application Priority Data

Aug. 26, 2014  (CN) .......................... 2014 1 0425269

(51) Int. Cl.
| | |
|---|---|
| *C05F 11/08* | (2006.01) |
| *C05F 17/00* | (2006.01) |
| *C05G 3/00* | (2006.01) |
| *C12P 7/08* | (2006.01) |
| *C12P 19/14* | (2006.01) |
| *C05F 11/10* | (2006.01) |
| *C05F 11/00* | (2006.01) |
| *C05G 3/04* | (2006.01) |

(52) U.S. Cl.
CPC .............. *C05F 11/08* (2013.01); *C05F 11/10* (2013.01); *C05F 17/0045* (2013.01); *C05G 3/00* (2013.01); *C05G 3/0064* (2013.01); *C12P 7/08* (2013.01); *C12P 19/14* (2013.01); *C05F 11/00* (2013.01); *C05G 3/04* (2013.01)

(58) Field of Classification Search
None
See application file for complete search history.

(56) References Cited

U.S. PATENT DOCUMENTS 3,513,857 A * 5/1970 Silberman .............. A24B 15/20
131/293

FOREIGN PATENT DOCUMENTS

| CN | 102139988 A | * | 8/2011 |
| CN | 102731176 A | * | 10/2012 |
| CN | 106148135 A | * | 11/2016 |

OTHER PUBLICATIONS

Yakult ("Products Information", Yakult Pharmaceutical Industry, available at https://www.yakult.co.jp/ypi/en/product.html, web capture from Jan. 31, 2010 provided courtesy of Wayback Internet Archive). (Year: 2010).*

* cited by examiner

*Primary Examiner* — Robert J Yamasaki
*Assistant Examiner* — Charles Zoltan Constantine
(74) *Attorney, Agent, or Firm* — Novoclaims Patent Services LLC; Mei Lin Wong

(57) ABSTRACT

The present invention relates to a composite microorganism enzyme, a method for preparing a plant nutrient solution by using the composite microorganism enzyme, and a fertilizer synergist. The method comprises the following steps: mixing fresh kelp pulp with a composite microorganism enzyme; and performing enzymolysis on the mixture of the fresh kelp pulp and the composite microorganism enzyme in an enzymolysis vessel to obtain the plant nutrient solution; the composite microorganism enzyme comprises more than one kind each of cellulase, pectinase, protease and amylase, the mass percentage of the cellulases and the pectinases being far greater than that of the proteases and the amylases. The present method for preparing a plant nutrient solution involves a simple enzymolysis process, mild reaction conditions, low costs and no other chemical compositions during the reaction processes, and maintains more of the active ingredients of the fresh kelp.

19 Claims, 3 Drawing Sheets

COMPOSITE MICROORGANISM ENZYME, METHOD FOR PREPARING PLANT NUTRIENT SOLUTION BY USING COMPOSITE MICROORGANISM ENZYME, AND FERTILIZER SYNERGIST

BACKGROUND OF THE PRESENT INVENTION

Field of Invention

The present invention relates to the field of biotechnology and plant nutrient, and more particularly to a method for producing a plant nutrient solution by using enzyme, and more particularly to a plant nutrient solution prepared by using seaweed.

Description of Related Arts

As technology has advanced nowadays to supply most of the basic human necessity needs such as food or sheltering in our country, there is a demand for high quality agricultural and nutrient food products in the society and in the field of agricultural production. Accordingly, the agriculture department launched a green-food program in 1990 to promote the production of pollution-free healthy food products. In the Green-food paper, the agriculture department mentioned that the development of green-food would have a deep impact on protecting the ecosystem, raising the agricultural products quality, enhancing the growth of food industry, improving people's heath and increasing exports of agriculture products. In the ten countermeasures for protection of ecological environment, the State Council has explicitly put forward the promotion of "ecological agriculture". In order to develop the ecological agriculture, pollution-free "green-food" is to be developed. The fertilization technology and the pesticide technology in the agricultural production must be reformed.

For a long time, the heavy use of chemical fertilizer and pesticide in farmland has increased the yield of crops but is subject to certain restrictions. The heavy use of fertilizer and pesticide causes the increasingly serious environmental pollution, soil compaction and crop resistance recession, thus resulting in a substantial increase in the use of pesticide and forming a vicious cycle. Therefore, there is an important demand to develop a new nutrient solution which can increase the crop production while greatly decreasing the use of fertilizer and pesticide to benefit the society and economy.

Plant nutrient solution which serves as a conditioning agent for promoting plant growth with a high efficiency works best in a relatively low concentration. Conventional plant growth conditioning agents are categorized as a type of pesticide which comprises a synthetic compound and natural plant hormone extracted from biological organism. Conventional plant growth condition agents include indole acetic acid, indole butyric acid, 1-naphthylacetic acid, naphthyloxyacetic acid, 4-chlophenoxyacetic acid, and gibberellic acid and etc. These are all synthetic plant hormone which are commonly used in agriculture. However, the pollution problem which is caused by the use of these synthetic plant hormones has become extremely serious social problem. Therefore, a pollution-free green promoter is needed in the green revolution. Conventional seaweed extraction technique involves the use of an alkaline solution for extraction and a concentrated and drying process under high temperature, which may easily destroy the natural active ingredients of seaweed. The method of microbial degradation to extract seaweed nutrient solution can meet the ecofriendly and pollution-free requirements while the destruction effect on the active ingredients of seaweed is small. Thus more active ingredients can be retained.

Chinese patent CN103145496A disclosed a method for preparing seaweed plant vegetative growth regulating agent. However, the method in the patent selected the use of cellulase, papain, and pectinase and there is not much difference in the use amount of cellulase, papain, and pectinase. Since protease is much more expensive than other enzyme, if the same amount of protease is required, the production cost will be increased, thus causing unnecessary waste of resources. In addition, this patent failed to address the problem of insufficient enzymatic hydrolysis.

SUMMARY OF THE PRESENT INVENTION

In view of the above mentioned problems of the conventional arts, the present invention discloses a method for preparing a plant nutrient solution. Fresh seaweed pulp and composite microbial enzyme are mixed and undergoes enzymatic hydrolysis, concentration under a thermal insulated condition in an enzymolysis tank to obtain the seaweed plant nutrient solution. The method of the present invention is simple while the seaweed nutrient solution has a relatively higher activity.

In one aspect of the present invention, the method for preparing the plant nutrient solution, characterized in that, the method comprises the following steps: mixing fresh seaweed pulp and composite microbial enzyme to form a mixture; and allowing enzymatic hydrolysis on the mixture of fresh seaweed pulp and composite microbial enzyme in an enzymolysis tank to obtain the plant nutrient solution, wherein the composite microbial enzyme comprises more than one enzyme selected from cellulase, pectinase, protease and amylase, wherein the cellulase is derived from *Trichoderma reesei*, *Trichoderma Viride*, and/or *Aspergillus Niger*, wherein the pectinase is derived from *Rhizopus Oryzae*, *Aspergillus Niger*, and/or *Aspergillus Oryzae*, wherein the protease is prepared by use of *Papain*, *Bromelain*, and/or *Bacillus Subtilis*, wherein the amylase is derived from *Bacillus Licheniformis*, *Aspergillus Oryzae*, and/or *Aspergillus Niger*;

wherein the mass percentage of the cellulase and the pectinase in the composite microbial enzyme is much greater than the mass percentage of the protease and/or the amylase.

According to a preferred embodiment of the present invention, the method for preparing the plant nutrient solution further comprises the following steps:

preparing fresh seaweed pulp, selecting mature fresh seaweed and removing inorganic impurities, then grinding after cutting the fresh seaweed to form seaweed pulps with granular size having a diameter below 50 μm;

placing the fresh seaweed pulps into a high speed dispersion kettle and adding water for the first time for mixing such that the water added and the fresh seaweed pulps can be thoroughly mixed together to form a mixture, wherein the mass ratio of the added water to the fresh seaweed pulp is (30-40):100;

placing the fresh seaweed pulps after mixing into an enzymolysis tank, adding water for the second time and adding composite microbial enzyme to form a mixture, wherein the mass ratio of the total water added from the first time and the second time to the fresh seaweed pulps is 50:100;

thoroughly mixing the mixture, then heating and maintaining a temperature for enzymatic hydrolysis, and during the process of enzymatic hydrolysis, stirring one time each hour and each time for 5 minutes; and processing solid-liquid separation for the mixture after enzymatic hydrolysis by recoil belt type filter machine, separating a serum after enzymatic hydrolysis and concentrating the serum under a condition of 60-68° C. to obtain the plant nutrient solution.

According to a preferred embodiment of the present invention, a mass percentages of the cellulase, the pectinase, the protease and amylase in the composite microbial enzyme are 60-100%, 0-40%, 0-5%, and 0-5% respectively; and an enzyme activity of the cellulase is $(18\text{-}24) \times 10^4$ μ/g,
an enzyme activity of the pectinase is $(2\text{-}5) \times 10^4$ μ/g,
an enzyme activity of the protease is $(10\text{-}50) \times 10^4$ μ/g,
an enzyme activity of the amylase is $(1\text{-}5) \times 10^4$ μ/g.

According to a preferred embodiment of the present invention, a mass ratio of the composite microbial enzyme to the fresh seaweed pulps is (0.3-3):100;

or a mass ratio of the composite microbial enzyme to the fresh seaweed pulps is (0.3-0.5):100;

or a mass ratio of the composite microbial enzyme to the fresh seaweed pulps is 0.4:100;

or a mass ratio of the composite microbial enzyme to the fresh seaweed pulps is (0.8-2.1):100;

or a mass ratio of the composite microbial enzyme to the fresh seaweed pulps is (0.82-2.85):100;

or a mass ratio of the composite microbial enzyme to the fresh seaweed pulps is (0.96-2.5):100;

or a mass ratio of the composite microbial enzyme to the fresh seaweed pulps is (1.2-2.35):100;

or a mass ratio of the composite microbial enzyme to the fresh seaweed pulps is (1.38-2.1):100;

or a mass ratio of the composite microbial enzyme to the fresh seaweed pulps is 1.5:100.

According to a preferred embodiment of the present invention, the enzymatic hydrolysis under thermal insulation condition of the water, the fresh seaweed pulps and the composite microbial enzyme is carried out for 12-60 hours under a temperature of 30-65° C.;

Or the enzymatic hydrolysis under thermal insulation condition of the water, the fresh seaweed pulps and the composite microbial enzyme is carried out under a temperature of 32-56° C.;

Or the enzymatic hydrolysis of the water, the fresh seaweed pulps and the composite microbial enzyme is carried out under a temperature of 42-62.5° C. and a thermal insulation condition;

Or the enzymatic hydrolysis of the water, the fresh seaweed pulps and the composite microbial enzyme is carried out under a temperature of 45-60° C. and a thermal insulation condition;

Or the enzymatic hydrolysis of the water, the fresh seaweed pulps and the composite microbial enzyme is carried out under a temperature of 48° C. and a thermal insulation condition;

Or the enzymatic hydrolysis of the water, the fresh seaweed pulps and the composite microbial enzyme is carried out under a temperature of 50-58° C. and a thermal insulation condition;

Or the enzymatic hydrolysis of the water, the fresh seaweed pulps and the composite microbial enzyme is carried out under a temperature of 55° C. and a thermal insulation condition;

Or the enzymatic hydrolysis of the water, the fresh seaweed pulps and the composite microbial enzyme is carried out under a temperature of 30-65° C. for 25-30 hours in a thermal insulation condition.

According to the preferred embodiment of the present invention, the enzymatic hydrolysis of the fresh seaweed pulps and the composite microbial enzyme is carried out under a pH of 3-7;

Or the enzymatic hydrolysis of the fresh seaweed pulps and the composite microbial enzyme is carried out under a pH of 4-5.5;

Or the enzymatic hydrolysis of the fresh seaweed pulps and the composite microbial enzyme is carried out under a pH of 3.5-5.5;

Or the enzymatic hydrolysis of the fresh seaweed pulps and the composite microbial enzyme is carried out under a pH of 3.2-5;

Or the enzymatic hydrolysis of the fresh seaweed pulps and the composite microbial enzyme is carried out under a pH of 3.2-4.5;

Or the enzymatic hydrolysis of the fresh seaweed pulps and the composite microbial enzyme is carried out under a pH of 3.5-4.5;

Or the enzymatic hydrolysis of the fresh seaweed pulps and the composite microbial enzyme is carried out under a pH of 5.5-6.5;

Or the enzymatic hydrolysis of the fresh seaweed pulps and the composite microbial enzyme is carried out under a pH of 5-6.

According to the preferred embodiment of the present invention, the mass ratio of the water added for the first time to the fresh seaweed pulps is 35:100.

According to the preferred embodiment of the present invention, the rotation frequency of the highspeed dispersion kettle after starting is 3000 rev/min, and the rotation frequency of the highspeed dispersion kettle is lowered from 3000 rev/min to 1000 rev/min after 3 minutes.

In another aspect of the present invention, the present invention discloses a composite microbial enzyme used in seaweed hydrolysis, wherein the microbial microbial enzyme comprises more than one kind each of cellulase, pectinase, protease and amylase, wherein the cellulase is derived from *Trichoderma reesei, Trichoderma viride*, and/or *Aspergillus niger*, wherein the pectinase is derived from *Rhizopus oryzae, Aspergillus niger*, and/or *Aspergillus oryzae*, wherein the protease is derived from *Papain, Bromelain*, and/or *Bacillus Subtilis*, wherein the amylase is derived from *Bacillus licheniformis, Aspergillus oryzae*, and/or *Aspergillus niger*.

In another aspect of the present invention, the present invention discloses a fertilizer synergist, characterized in that, the fertilizer synergist comprises the composite microbial enzyme as mentioned above, or the plant nutrient solution which is prepared by the method disclosed above.

Comparing to conventional arts, the present invention has the following advantages:

1. The enzymatic hydrolysis process is simple, the reaction requirements is mild, the cost is low, no other chemical compositions are used during the reaction process, and the reaction condition is pollution-free to the environment;

2. Higher level of active ingredients of the fresh seaweeds is retained, the active ingredients in the fresh seaweeds is not destroyed in the process of enzymatic hydrolysis under a mild condition;

3. The composition of the composite enzyme being selected enhance the enzymatic hydrolysis of fresh seaweeds so that the different natural active ingredients in the seaweeds can be degraded and then absorbed by crops easily.

4. The plant nutrient solution is a kind of green ecofriendly nutrient solution which does not introduce any environmental pollution during its use on the plant.

DETAILED DESCRIPTION OF THE PREFERRED EMBODIMENT

The following provides a detailed description of the present invention with the preferred embodiments:

1. Process of selection of composite microbial enzyme of the present invention.

The composite microbial enzyme of the present invention comprises a plurality of enzyme which includes cellulase, pectinase, protease and amylase. The composite microbial enzyme uses cellulase and pectinase as the main enzyme species while protease and amylase are used as the secondary enzyme species. In particular, the cellulase produced by *Trichoderma reesei*, *Trichoderma Viride*, or *Aspergillus Niger* is selected; the pectinase produced by *Rhizopus Oryzae*, *Aspergillus Niger* or *Aspergillus Oryzae* is selected; the protease produced by Papain, Bromelain, or *Bacillus Subtilis* is selected; the amylase produced by *Bacillus Licheniformis*, *Aspergillus Oryzae*, or *Aspergillus Niger* is selected.

The above mentioned enzyme producing bacteria or plant can be used as a source of microorganism or plant in food additives.

Wherein, the enzyme activity of the selected cellulase is $(18-24) \times 10^4$ μ/g, the the enzyme activity of the selected pectinase is $(2-5) \times 10^4$ μ/g, the enzyme activity of the selected protease is $(10-50) \times 10^4$ μ/g, and the amylase activity is $(1-5) \times 10^4$ μ/g.

Figure 1:
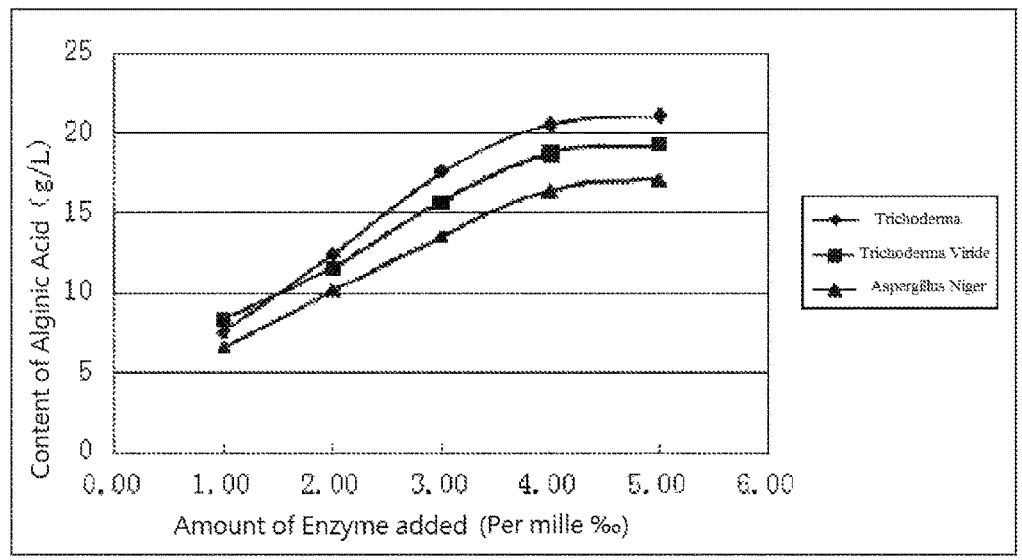
FIG. 1 is an illustration of the hydrolysis effect of the cellulase amongst the composite microbial enzyme produced by different strains according to method of preparation of the plant nutrient solution of the present invention.

The followings provide provides a detailed description of the selection of composite enzyme based on the accompanying drawings:

FIG. 1 of the drawings illustrates the hydrolytic effect of the cellulase produced by different strains which include *Trichoderma reesei*, *Trichoderma Viride*, or *Aspergillus Niger*. The standard of hydrolysis effect is measured by the amount of alginic acid released. Among the different strains, the hydrolysis effect of cellulase produced by *Trichoderma reesei* achieves the best result. For *Trichoderma reesei*, with the addition of enzyme from 1% to 5%, the content of alginic acid from hydrolysis is 8 g/L~22 g/L. For the cellulase produced by *Trichoderma viride*, with the addition of enzyme from 1% to 5%, the content of alginic acid from hydrolysis is 9 g/L~19.5 g/L. For the cellulase produced by *Aspergillus Niger*, with the addition of enzyme from 1% to 5%, the content of alginic acid from hydrolysis is 7 g/L~17 g/L. Accordingly, cellulase derived from *Trichoderma reesei* is the preferred selection for the cellulase of the composite microbial enzyme of the present invention. Of course, the cellulose produced by *Trichoderma Viride* and *Aspergillus Niger* is also feasible.

Figure 2:
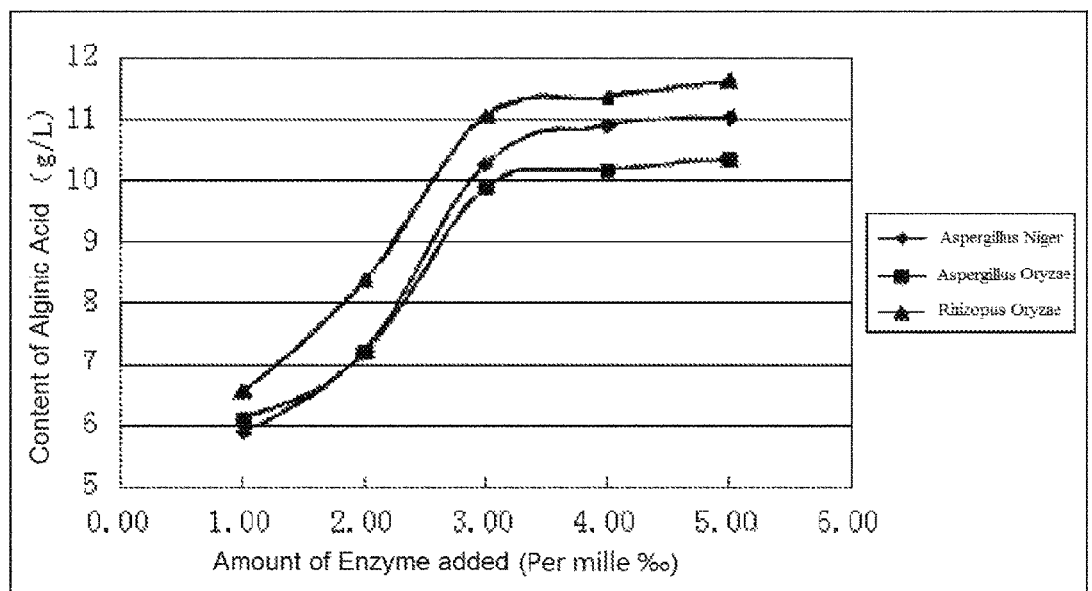
FIG. 2 is an illustration of the hydrolysis effect of the pectinase amongst the composite microbial enzyme produced by different strains according to method of preparation of the plant nutrient solution of the present invention.

FIG. 2 of the drawings illustrates the hydrolytic effect of the pectinase produced by different strains which includes *Aspergillus Niger*, *Aspergillus Oryzae*, or *Rhizopus Oryzae*. The standard of hydrolysis effect is measured by the amount of alginic acid released. Among the different strains, the hydrolysis effect of pectinase produced by *Rhizopus Oryzae* achieves the best result. For the pectinase produced by *Rhizopus Oryzae*, with the addition of enzyme from 1% to 5%, the content of alginic acid from hydrolysis is 6.5 g/L~11.6 g/L. For the pectinase produced by *Aspergillus Niger*, with the addition of enzyme from 1% to 5%, the content of alginic acid from hydrolysis is 5.9 g/L~11 g/L. For the pectinase produced by *Aspergillus Oryzae*, with the addition of enzyme from 1% to 5%, the content of alginic acid from hydrolysis is 6.1 g/L~13 g/L. Accordingly, pectinase derived from *Rhizopus Oryzae* is the preferred selection for the pectinase of the composite microbial enzyme of the present invention. Of course, the pectinase produced by *Aspergillus Niger* and *Aspergillus Oryzae* is also feasible.

Figure 3:
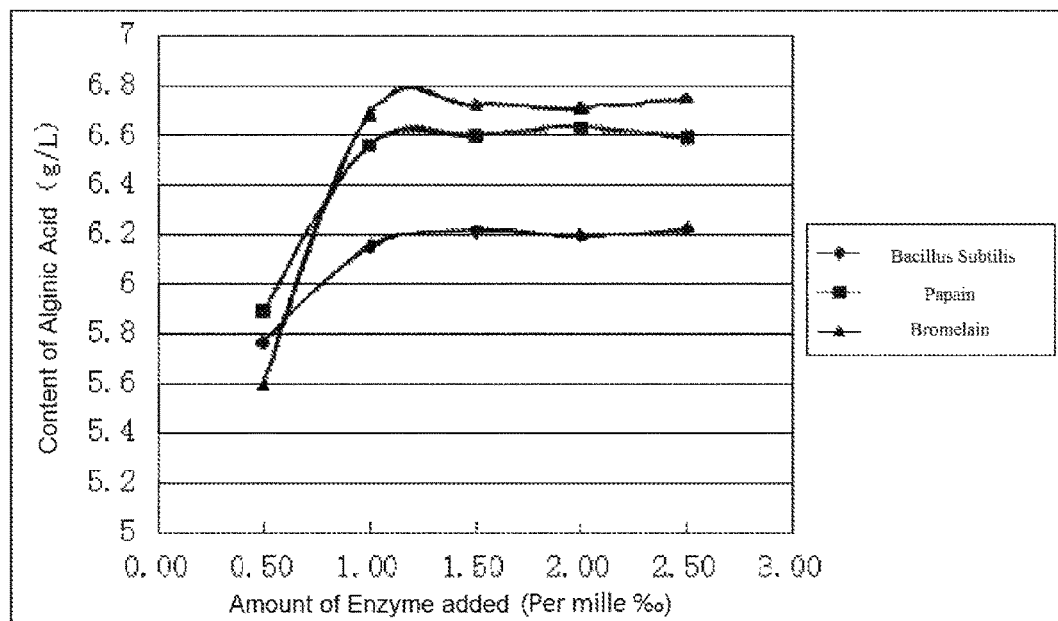
FIG. 3 is an illustration of the hydrolysis effect of the protease amongst the composite microbial enzyme produced by different strains according to method of preparation of the plant nutrient solution of the present invention.

FIG. 3 of the drawings illustrates the hydrolytic effect of the protease produced by different strains which include *Bacillus Subtilis*, Papain, or Bromelain. The standard of hydrolysis effect is measured by the amount of alginic acid released. Among the different strains, the hydrolysis effect of protease produced by Bromelain achieves the best result. For the protease produced by Bromelain, with the addition of enzyme from 0.5% to 2.5%, the content of alginic acid from hydrolysis is 5.58 g/L~6.8 g/L; when the addition of enzyme exceeds 1%, the content of alginic acid from hydrolysis decreases to 6.7 g/L and then tends to balance. For the protease produced by Papain, with the addition of enzyme from 0.5% to 2.5%, the content of alginic acid from hydrolysis is 5.89 g/L~6.6 g/L. For the protease produced by *Bacillus Subtilis*, with the addition of enzyme from 0.5% to 2.5%, the content of alginic acid from hydrolysis is 5.78 g/L~6.2 g/L. Accordingly, protease derived from Bromelain is the preferred selection for the protease of the composite microbial enzyme of the present invention. Of course, the protease produced by Papain and *Bacillus Subtilis* is also feasible.

Figure 4:
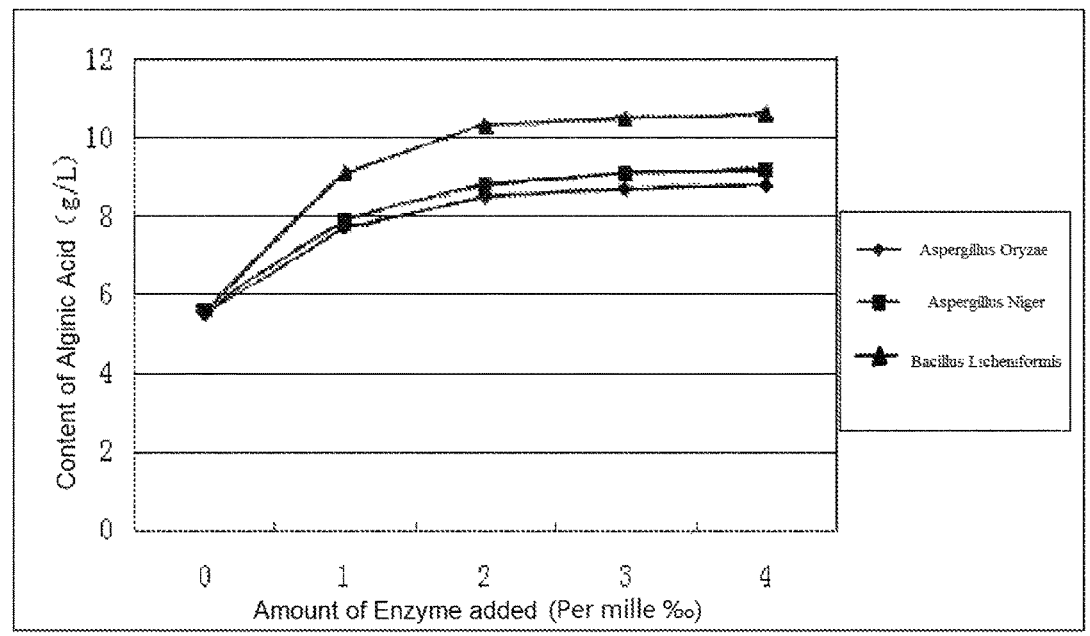
FIG. 4 is an illustration of the hydrolysis effect of the amylase amongst the composite microbial enzyme produced by different strains according to method of preparation of the plant nutrient solution of the present invention.

FIG. 4 of the drawings illustrates the hydrolytic effect of the amylase produced by different strains which include *Aspergillus Niger*, *Aspergillus Oryzae*, or *Bacillus Licheniformis*. The standard of hydrolysis effect is measured by the amount of alginic acid released. Among the different strains, the hydrolysis effect of amylase produced by *Bacillus Licheniformis* achieves the best result. For the amylase produced by *Bacillus Licheniformis*, with the addition of enzyme from 1% to 4%, the content of alginic acid from hydrolysis is 5.6 g/L~10.6 g/L. For the amylase produced by *Aspergillus Oryzae*, with the addition of enzyme from 1% to 4%, the content of alginic acid from hydrolysis is 5.5 g/L~8.8 g/L. For the amylase produced by *Aspergillus*

*Niger*, with the addition of enzyme from 1% to 4%, the content of alginic acid from hydrolysis is 5.6 g/L~9.2 g/L. Accordingly, amylase derived from *Bacillus Licheniformis* is the preferred selection for the amylase of the composite microbial enzyme of the present invention. Of course, the amylase produced by *Aspergillus Niger* and *Aspergillus Oryzae* and is also feasible.

According to a preferred embodiment of the present invention, the composite microbial enzyme is selected from more than one of the cellulase produced by *Trichoderma reesei*, the pectinase produced by *Rhizopus Oryzae*, protease from Bromelain and the amylase produced by *Bacillus Licheniformis*. This selected preferred embodiment of composite enzyme can yield a more thorough and complete degradation of the fresh seaweed such that the content of active ingredients in the seaweed plant nutrient solution from enzymatic hydrolysis is higher, which is more easily absorbed and utilized by plant.

2. Composition ratio of the composite microbial enzyme of the present invention.

The composite enzyme of the present invention is primarily comprised of cellulase, and then secondly comprised of pectinase, and thirdly comprised of protease, and lastly comprised of amylase. Wherein, mass percentages of the cellulase and the pectinase in the composite enzyme are far greater than those of the protease and the amylase. According to the preferred embodiment of the present invention, which has relatively better hydrolysis effect on fresh seaweeds, the mass percentages of the composite microbial enzyme are: cellulase 60~100%, pectinase 0~40%, protease 0~5%, and amylase 0-5%. Table 1 lists the embodiments of the composite enzyme with different mass percentages.

TABLE 1

| Embodiment | mass ratio of enzyme | | | | | |
|---|---|---|---|---|---|---|
| | 1 | 2 | 3 | 4 | 5 | 6 |
| cellulase | 100% | 60% | 60% | 60% | 70% | 60% |
| | 200000 μ/g | 120000 μ/g | 120000 μ/g | 120000 μ/g | 140000 μ/g | 120000 μ/g |
| pectinase | 0 | 40% | 35% | 35% | 27% | 30% |
| | | 12000 μ/g | 10500 μ/g | 10500 μ/g | 8100 μ/g | 8100 μ/g |
| protease | 0 | 0 | 5% | 0 | 3% | 5% |
| | | | 25000 μ/g | | 15000 μ/g | 25000 μ/g |
| amylase | 0 | 0 | 0 | 5% | 0 | 5% |
| | | | | 2500 μ/g | | 2500 μ/g |
| Alginic acid g/L | 17.25 | 19.56 | 21.32 | 19.62 | 22.35 | 23.20 |

Embodiment 1

The composite microbial enzyme comprises 100% cellulose, wherein the cellulase activity of the cellulose is 200000 μ/g. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 17.25 g/L.

Embodiment 2

The composite microbial enzyme comprises 60% cellulase and 40% pectinase, wherein the cellulase activity of the selected cellulase is 120000 μ/g and the enzyme activity of the selected pectinase is 12000 μ/g. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 19.56 g/L.

Embodiment 3

The composite microbial enzyme comprises 60% cellulase, 35% pectinase and 5% protease, wherein the enzyme activity of the cellulase is 120000 μ/g, the enzyme activity of the pectinase is 10500 μ/g and the enzyme activity of the protease is 25000 μlg. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 21.32 g/L.

Embodiment 4

The composite microbial enzyme comprises 60% cellulase, 35% pectinase and 5% amylase, wherein the enzyme activity of the cellulase is 120000 μ/g, the enzyme activity of the pectinase is 10500μ/g and the enzyme activity of the amylase is 2500 μlg. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 19.62 g/L.

Embodiment 5

The composite microbial enzyme comprises 70% cellulase, 27% pectinase and 3% protease, wherein the enzyme activity of the cellulase is 140000 μ/g, the enzyme activity of the pectinase is 8100μ/g and the enzyme activity of the protease is 15000μ/g. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 22.35 g/L.

Embodiment 6

The composite microbial enzyme comprises 60% cellulase, 30% pectinase, 5% protease and 5% amylase, wherein the enzyme activity of the cellulase is 120000μ/g, the enzyme activity of the pectinase is 8100μ/g, the enzyme activity of the protease is 25000 μ/g, and the enzyme activity of the amylase is 2500 μlg. Obtain 100 ml of seaweed pulps, add the composite microbial enzyme according to the liquid mass ratio of composite microbial enzyme to seaweed pulps of 0.4% to obtain a mixture solution, carry out enzymatic hydrolysis under thermal insulation condition for 18 hours, the content of alginic acid in the supernatant is 23.20 g/L.

According to the results as shown from embodiments 1-6 for the degradation effect of the composite microbial enzyme on fresh seaweed (the effect of enzymatic hydrolysis is measured by the amount of alginic acid released), it can be seen that the composite microbial enzyme yields a better enzymatic hydrolysis result in comparison to using a single enzyme. Other than cellulose and crude protein, fresh seaweed also contains seaweed polysaccharide which comprises sodium alginate, fucoidan, and alginate starch. Wherein alginate starch is a type of polysaccharide inside a cell which is mainly composed of β-1, 3-D-glucan group. The long chain polymer has a small amount of β-1, 6 glucosidicbond between chain and their amount is about 1% in the seaweed. Therefore, the composite microbial enzyme uses amylase as an auxiliary enzyme such that the enzymatic hydrolysis for the seaweed is more efficient. In addition, the amount of crude protein in seaweed is from 5-9%, which is a relatively low amount. The cost of using protease is the highest among all of the above mentioned enzymes. Therefore, it is not cost efficient if the use amount of protease is equal to other enzymes. In view of the above, the mass percentages of the cellulase and pectinase are far greater than those of protease and amylase. Table 1 shows that the hydrolysis effect of the composite microbial enzyme as formulated in embodiment 6 on fresh seaweed pulp is the best. Accordingly, the composition of the composite microbial enzyme in the embodiment 6 is the most preferred embodiment.

Figure 5:
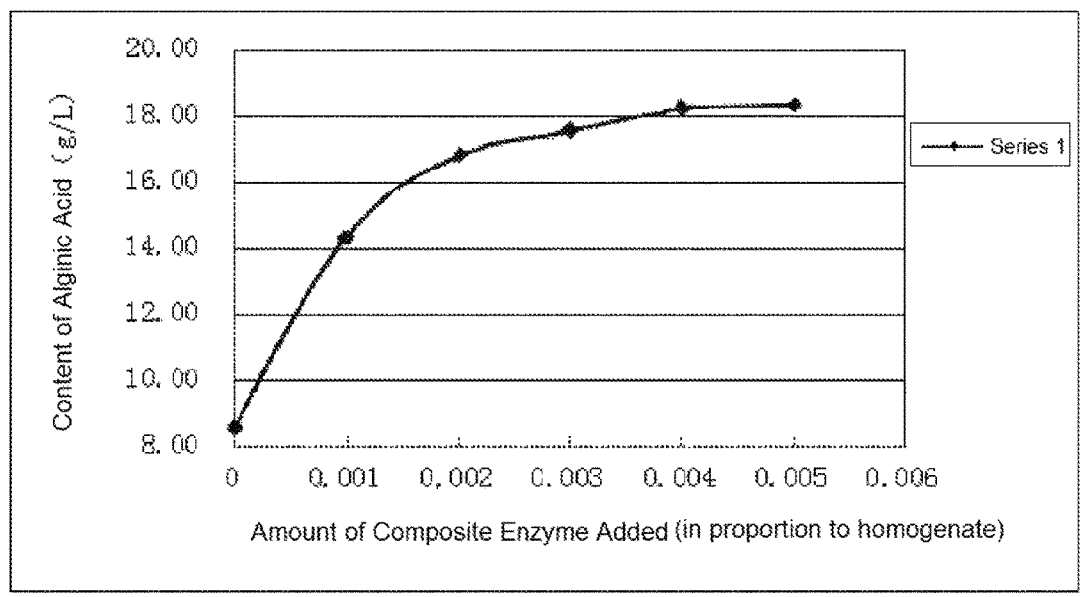
FIG. 5 is an illustration of the effect of the amount of water added to the composite microbial enzyme on hydrolysis according to method of preparation of the plant nutrient solution of the present invention.

FIG. 5 of the drawings illustrates the effect of the amount of water added to the composite microbial enzyme on hydrolysis. The enzyme mass ratio percentage of this experiment is based on the composition of the embodiment 6 in which the composition of the composite microbial enzyme is the most preferred embodiment. With the addition of the composite microbial enzyme changes from 0-0.06%, the content of alginic acid increases gradually. While when the addition of the composite microbial enzyme changes from 0% to 0.3%, the content of alginic acid increases roughly linearly. When the addition of the composite microbial enzyme is 0.3%, the content of alginic acid is 17.95 g/L. When the addition of the composite microbial enzyme reaches 0.4%, the content of alginic acid reaches 18.32 g/L. When the addition of the composite microbial enzyme exceeds 0.4%, the content of alginic acid tends to be level and does not increase further. In view of the above, the preferred addition amount of the composite microbial enzyme of the present invention is selected to be 0.3% 0.4%.

Determine the parameters for enzymatic hydrolysis of the present invention.

Table 2 lists different factors such as the reaction temperature, the amount of enzyme added, the pH and the hydrolysis time in the process of enzymatic hydrolysis of the composite microbial enzyme of the present invention. Table 3 illustrates the results analysis of the orthogonal test

TABLE 2

Level Coding Table for Different factors of Orthogonal test.

| | factor | | |
| --- | --- | --- | --- |
| level | Temperature (° C.) A | Amount of Enzyme (%) B | pH C |
| 1 | 50 | 0.3 | 5.0 |
| 2 | 55 | 0.4 | 5.5 |
| 3 | 60 | 0.5 | 6.0 |

TABLE 3

Orthogonal test results

| Embodiments | Temp (° C.) | Enzyme (%) | pH | Alginic acid content (g/L) | | | |
| --- | --- | --- | --- | --- | --- | --- | --- |
| | | | | I | II | III | Average |
| 7 | A1 | B1 | C2 | 15.35 | 14.98 | 15.13 | 15.15 |
| 8 | A1 | B2 | C1 | 17.05 | 16.89 | 17.13 | 17.02 |
| 9 | A1 | B3 | C3 | 18.56 | 19.01 | 18.75 | 18.77 |
| 10 | A2 | B1 | C1 | 17.99 | 18.24 | 18.13 | 18.12 |
| 11 | A2 | B2 | C2 | 23.22 | 22.83 | 22.53 | 22.86 |
| 12 | A2 | B3 | C3 | 21.89 | 21.55 | 22.15 | 21.86 |
| 13 | A3 | B1 | C3 | 20.88 | 21.51 | 21.23 | 21.21 |
| 14 | A3 | B2 | C1 | 21.15 | 20.33 | 20.47 | 20.65 |
| 15 | A3 | B3 | C2 | 21.26 | 20.89 | 21.33 | 21.16 |

Obtain 2700 ml of fresh seaweed pulps, divide into 27 250 ml conical flasks, each flask contains 100 ml. Three of these as a group are to be carried out the orthogonal test for each of the embodiments 7-15. The three samples in each group is used for testing based on each embodiment. After enzymatic hydrolysis, the content of alginic acid in the supernatant is determined. In each embodiment, the content of alginic acid is the average value of the content of alginic acid of the three samples. From Table 3, embodiment 11 is the most preferred embodiment for the different factors.

Embodiment 16

Obtain 15 L of fresh seaweed pulps and add to an enzymolysis tank, then add the composite microbial enzyme, wherein the composite microbial enzyme has a composition based on the mass ratio in the embodiment 6. Utilize the parameters in the embodiment 11 to set the reaction temperature, addition amount of the composite microbial enzyme and pH value. After hydrolysis, the average content of alginic acid recorded is 23.2 g/L.

Figure 6:
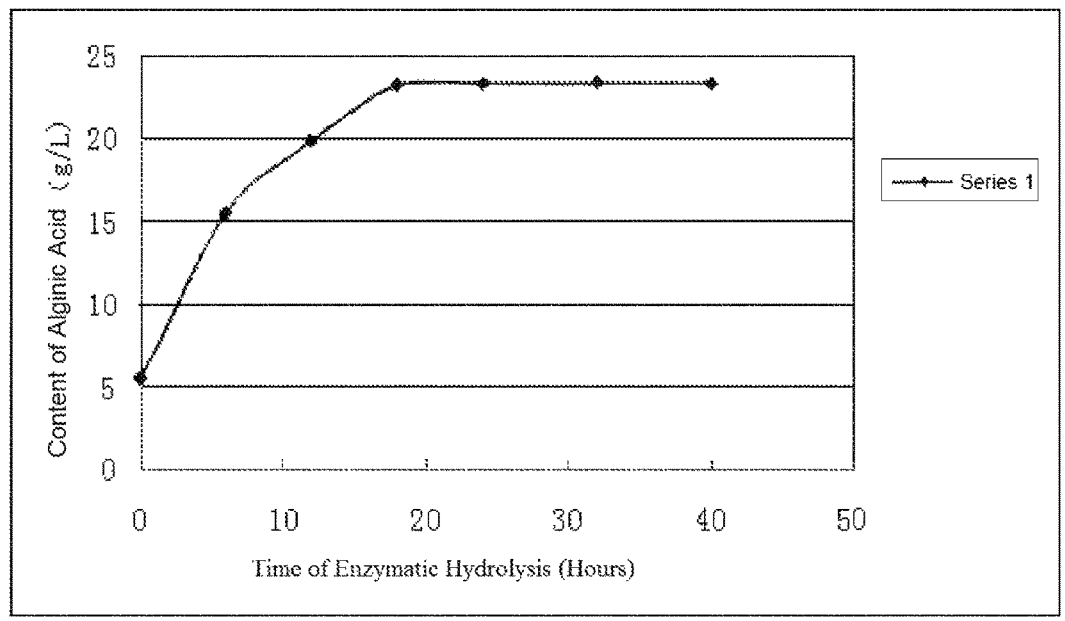
FIG. 6 is an illustration of the effect of time on hydrolysis of the composite microbial enzyme on according to method of preparation of the plant nutrient solution of the present invention.

FIG. 6 shows the effect of time on enzymatic hydrolysis of the composite microbial enzyme when the temperature is 55° C., the addition amount of composite microbial enzyme is 0.4% and the pH is 5.5. As the time of enzymatic hydrolysis increases, the content of alginic acid increases gradually. While when the time changes from 0-20 hours, the content of alginic acid increases roughly linearly. When the time reaches 12 hours, the content of alginic acid is 20 g/L. When the time reaches 18 hours, the content of alginic acid reaches the maximum, which is 23 g/L. After this, as the time for hydrolysis increases, the content of alginic acid tends to be level and remains unchanged. In view of cost consideration, the preferred time for enzymatic hydrolysis is 18 hours.

In another aspect of the present invention, the present invention discloses a method for preparing a plant nutrient solution. The method is described as follows:

1. prepare fresh seaweed pulp, select mature fresh seaweed and remove inorganic impurities through rinsing and soaking with fresh water, then soak after shearing the fresh seaweed to form seaweed pulps with granular size having a diameter below 50 μm.

2. Place the fresh seaweed pulps into a high speed dispersion kettle and add water for the first time for mixing such that the water added and the fresh seaweed pulps can be thoroughly mixed together, wherein the mass ratio of the water added to the fresh seaweed pulp is (30-40):100. Preferably, the mass ratio of the water added to the fresh seaweed pulp is 35:100. According to a preferred embodiment of the present invention, the rotation frequency of the highspeed dispersion kettle after starting is 3000 rev/min, and the rotation frequency of the highspeed dispersion kettle is lowered from 3000 rev/min to 1000 rev/min after 3 minutes.

3. Placing the fresh seaweed pulps after mixing into an enzymolysis tank, add water for the second time and add the composite microbial enzyme for mixing the fresh seaweed and the composite microbial enzyme to form a mixture, wherein the mass ratio of the total water added from the first time and the second time to the fresh seaweed pulps is 50:100.

4. Mix the mixture thoroughly, then heating and maintaining a temperature for enzymatic hydrolysis. During the process of enzymatic hydrolysis, stir one time each hour and each time for 5 minutes.

5. Process solid-liquid separation for the mixture after enzymatic hydrolysis by recoil belt type filter machine, separate a serum after enzymatic hydrolysis and concentrate the serum under a condition of 60-68° C. to obtain the plant nutrient solution.

Wherein the method for preparing a plant nutrient solution disclosed in the present invention selects the composite microbial enzyme as mentioned above. According to a plurality of preferred embodiments, the mass ratio of the composite microbial enzyme to the fresh seaweed are: (0.3-3):100, (0.3-0.5):100, 0.4:100, (0.8-2.1):100, (0.82-2.85):100, (0.96-2.5):100, (1.2-2.35):100, (1.38-2.1):100 or 1.5:100. The preferred mass ratio is 0.4:100.

Based on a plurality of embodiments according to the method for preparing a plant nutrient solution of the present invention, the water, the fresh seaweed pulps and the composite microbial enzyme undergoes a thermal insulated enzymatic hydrolysis which takes place for 12-60 hours under the temperature of 30° C.-65° C.; or the water, the fresh seaweed pulps and the composite microbial enzyme undergoes a thermal insulated enzymatic hydrolysis under the temperature of 32° C.-56° C.; or the water, the fresh seaweed pulps and the composite microbial enzyme undergoes a thermal insulated enzymatic hydrolysis under the temperature of 42° C.-62.5° C.; or the water, the fresh seaweed pulps and the composite microbial enzyme undergoes a thermal insulated enzymatic hydrolysis under the temperature of 45° C.-60° C.; or the water, the fresh seaweed pulps and the composite microbial enzyme undergoes a thermal insulated enzymatic hydrolysis under the temperature of 48° C.; or the water, the fresh seaweed pulps and the composite microbial enzyme undergoes a thermal insulated enzymatic hydrolysis under the temperature of 50° C.-58° C.; or the water, the fresh seaweed pulps and the composite microbial enzyme undergoes a thermal insulated enzymatic hydrolysis under the temperature of 55° C.; or the water, the fresh seaweed pulps and the composite microbial enzyme undergoes a thermal insulated enzymatic hydrolysis which takes place for 25-30 hours under the temperature of 30° C.-65° C. The preferred embodiment is that the water, the fresh seaweed pulps and the composite microbial enzyme undergoes a thermal insulated enzymatic hydrolysis which takes place for 18 hours under the temperature of 55° C.

According to a plurality of embodiments of the present invention, the pH for enzymatic hydrolysis is 3~7, 3~7, 4~5.5, 3.5~5.5, 3.2~5, 3.5~4.5, 5.5~6.5, or 5~6. In the preferred embodiment, the pH for enzymatic hydrolysis of fresh seaweed pulps and composite microbial enzyme is 4~5.5.

Embodiment 17

According to a preferred embodiment, the present invention discloses a method for preparing a plant nutrient solution, the method comprises the steps of:

1. prepare fresh seaweed pulp, select mature fresh seaweed and remove inorganic impurities through rinsing and soaking with fresh water, then soak after shearing the fresh seaweed to form seaweed pulps with granular size having a diameter below 50 μm.

Place the fresh seaweed pulps into a high speed dispersion kettle and add water for the first time for mixing such that the water added and the fresh seaweed pulps can be thoroughly mixed together, wherein the mass ratio of the water added to the fresh seaweed pulp is 35:100. The rotation frequency of the highspeed dispersion kettle after starting is 3000 rev/min, and the rotation frequency of the highspeed dispersion kettle is lowered from 3000 rev/min to 1000 rev/min after 3 minutes.

3. Placing the fresh seaweed pulps after mixing into an enzymolysis tank, add water for the second time and add the composite microbial enzyme for mixing the fresh seaweed and the composite microbial enzyme to form a mixture, wherein the mass ratio of the total water added from the first time and the second time to the fresh seaweed pulps is 50:100. Wherein the mass ratio of the selected composite microbial enzyme to the fresh seaweed is 0.4%. The selected composite microbial enzyme is formulated by a mixture of 60% cellulase, 30% pectinase, 5% protease and 5% amylase by percentage mass.

5. Process solid-liquid separation for the mixture after enzymatic hydrolysis by recoil belt type filter machine, separate a serum after enzymatic hydrolysis and concentrate the serum under a condition of 60-68° C. to obtain the plant nutrient solution.

According to another aspect of the present invention, the present invention also discloses a composite microbial enzyme used in seaweed hydrolysis. The composite microbial enzyme comprises more than one kind each of cellulase, pectinase, protease, and amylase and is prepared by the above mentioned preparation method.

According to another aspect of the present invention, the present invention also discloses a fertilizer synergist, characterizes in that, the fertilizer synergist comprises the above mentioned composite microbial enzyme, or the fertilizer synergist comprises the plant nutrient solution as mentioned above and is prepared by the above preparation method.

It is worth mentioning that the above embodiments are for exemplary illustration only. One skilled in the art can derive different technical solutions which is based on the present invention while these technical solutions also fall within the scope of the present invention. One skilled in the art will understand that the embodiment of the present invention as shown in the drawings and described above is exemplary only and not intended to be limiting. The scope of protection provided by the present invention is limited by the claims and its equivalences.

What is claimed is:

1. A method of preparing a plant nutrient solution comprising the following steps of:
preparing fresh seaweed pulp, selecting mature fresh seaweed and removing inorganic impurities, then grinding after cutting the fresh seaweed to form seaweed pulps with granular size having a diameter below 50 μm;
placing the fresh seaweed pulps into a high speed dispersion kettle and adding water for the first time for mixing such that the water added and the fresh seaweed pulps can be thoroughly mixed together to form a mixture, wherein the mass ratio of the added water to the fresh seaweed pulp is in the range of 30:100 to 40:100;
placing the fresh seaweed pulps after mixing into an enzymolysis tank, adding water for the second time and adding composite microbial enzyme to form a mixture, wherein the mass ratio of the total water added from the first time and the second time to the fresh seaweed pulps is 50:100, wherein the composite microbial enzyme comprises more than one class of enzyme selected from the group consisting of cellulase, pectinase, protease and amylase, wherein the cellulase is sourced from *Trichoderma reesei, Trichoderma Viride*, and/or *Aspergillus Niger*; wherein the pectinase is sourced from *Rhizopus Oryzae, Aspergillus Niger*, and/or *Aspergillus Oryzae*; wherein the protease is sourced from Papain, Bromelain, and/or *Bacillus Subtilis*; wherein the amylase is sourced from *Bacillus Licheniformis, Aspergillus Oryzae*, and/or *Aspergillus Niger*, wherein a mass percentage of the cellulase and the pectinase in the composite microbial enzyme are much greater than a mass percentage of the protease and/or the amylase;
thoroughly mixing the mixture, then heating and maintaining a temperature for enzymatic hydrolysis, and during the process of enzymatic hydrolysis, stirring one time each hour and each time for 5 minutes; and
processing solid-liquid separation for the mixture after enzymatic hydrolysis by recoil belt type filter machine, separating a serum after enzymatic hydrolysis and concentrating the serum at 60-68° C. to obtain the plant nutrient solution.

2. The method of preparing a plant nutrient solution according to claim 1, characterized in that, mass percentages of the cellulase, the pectinase, the protease and the amylase in the composite microbial enzyme are 60-100%, 0-40%, 0-5%, and 0-5% respectively.

3. The method of preparing a plant nutrient solution according to claim 1, characterized in that, a mass ratio of the composite microbial enzyme to the fresh seaweed pulps is in the range of 0.3:100 to 3:100.

4. The method of preparing a plant nutrient solution according to claim 3, characterized in that, the enzymatic hydrolysis under thermal insulation condition of the water, the fresh seaweed pulps and the composite microbial enzyme is carried out for 12-60 hours at a temperature of 30-65° C.;
if the enzymatic hydrolysis of the water, the fresh seaweed pulps and the composite microbial enzyme is carried out at a temperature of 30-65° C. the enzymatic hydrolysis is carried out for 25-30 hours.

5. The method of preparing a plant nutrient solution according to claim 4, characterized in that, the enzymatic hydrolysis of the fresh seaweed pulps and the composite microbial enzyme is carried out at a pH of 3-7.

6. The method of preparing a plant nutrient solution according to claim 1, characterized in that, a mass ratio of the water added for the first time to the fresh seaweed pulps is 35:100.

7. The method of preparing a plant nutrient solution according to claim 1, characterized in that, a rotation frequency of the highspeed dispersion kettle after starting is 3000 rev/min, and a rotation frequency of the highspeed dispersion kettle is lowered from 3000 rev/min to 1000 rev/min after 3 minutes.

8. The method of preparing a plant nutrient solution according to claim 1, characterized in that, a mass ratio of the composite microbial enzyme to the fresh seaweed pulps is 0.4:100.

9. The method of preparing a plant nutrient solution according to claim 8, characterized in that, the enzymatic hydrolysis under thermal insulation condition of the water, the fresh seaweed pulps and the composite microbial enzyme is carried out for 12-60 hours at a temperature of 30-65° C.

10. The method of preparing a plant nutrient solution according to claim 9, characterized in that, the enzymatic hydrolysis of the fresh seaweed pulps and the composite microbial enzyme is carried out at a pH of 3-7.

11. The method of preparing a plant nutrient solution according to claim 1, characterized in that, a mass ratio of the composite microbial enzyme to the fresh seaweed pulps is in the range of 0.82:100 to 2.1:100.

12. The method of preparing a plant nutrient solution according to claim 11, characterized in that, the enzymatic hydrolysis under thermal insulation condition of the water, the fresh seaweed pulps and the composite microbial enzyme is carried out for 12-60 hours at a temperature of 30-65° C.

13. The method of preparing a plant nutrient solution according to claim 12, characterized in that, the enzymatic hydrolysis of the fresh seaweed pulps and the composite microbial enzyme is carried out at a pH of 3-7.

14. The method of preparing a plant nutrient solution according to claim 1, characterized in that, a mass ratio of the composite microbial enzyme to the fresh seaweed pulps is in the range of 0.96:100 to 2.5:100.

15. The method of preparing a plant nutrient solution according to claim 14, characterized in that, the enzymatic hydrolysis under thermal insulation condition of the water, the fresh seaweed pulps and the composite microbial enzyme is carried out for 12-60 hours at a temperature of 30-65° C.

16. The method of preparing a plant nutrient solution according to claim 15, characterized in that, the enzymatic hydrolysis of the fresh seaweed pulps and the composite microbial enzyme is carried out at a pH of 3-7.

17. The method of preparing a plant nutrient solution according to claim 1, characterized in that, a mass ratio of the composite microbial enzyme to the fresh seaweed pulps is 1.5:100.

18. The method of preparing a plant nutrient solution according to claim 17, characterized in that, the enzymatic hydrolysis under thermal insulation condition of the water, the fresh seaweed pulps and the composite microbial enzyme is carried out for 12-60 hours at a temperature of 30-65° C.

19. The method of preparing a plant nutrient solution according to claim 18, characterized in that, the enzymatic hydrolysis of the fresh seaweed pulps and the composite microbial enzyme is carried out at a pH of 3-7.

* * * * *